United States Patent [19]

Weber et al.

[11] 4,333,944
[45] Jun. 8, 1982

[54] 8-HALO-6-PHENYL-4H-S-TRIAZOLO (3,4-C) THIENO 1,4-DIAZEPIN-1-ONES

[75] Inventors: Karl-Heinz Weber, Gau-Algesheim; Adolf Langbein, Ingelheim am Rhein; Erich Lehr, Waldalgesheim; Karin Böke, Ingelheim am Rhein; Franz J. Kuhn, Bingen, all of Fed. Rep. of Germany

[73] Assignee: Boehringer Ingelheim GmbH, Ingelheim am Rhein, Fed. Rep. of Germany

[21] Appl. No.: 233,294

[22] Filed: Feb. 10, 1981

Related U.S. Application Data

[63] Continuation of Ser. No. 101,232, Dec. 7, 1979, abandoned, which is a continuation of Ser. No. 41,941, May 24, 1979, abandoned, which is a continuation of Ser. No. 881,851, Feb. 27, 1978, abandoned.

[30] Foreign Application Priority Data

Feb. 25, 1977 [DE] Fed. Rep. of Germany ....... 2708121

[51] Int. Cl.³ .................... A61K 31/55; C07D 495/14
[52] U.S. Cl. ................. 424/269; 260/245.5; 260/330
[58] Field of Search ...................... 260/245.5; 424/269

[56] References Cited

U.S. PATENT DOCUMENTS

| | | | |
|---|---|---|---|
| 3,646,055 | 2/1972 | Hester et al. | 260/245.5 |
| 3,965,111 | 6/1976 | Nakanishi et al. | 260/245.5 |
| 4,094,984 | 6/1978 | Weber et al. | 260/245.5 |
| 4,155,913 | 5/1979 | Hellerbach et al. | 260/245.5 |

FOREIGN PATENT DOCUMENTS

| | | | |
|---|---|---|---|
| 2405682 | 8/1974 | Fed. Rep. of Germany | 260/245.5 |
| 2708121 | 9/1978 | Fed. Rep. of Germany | 424/269 |
| 7502391 | 9/1975 | Netherlands | 260/245.5 |

Primary Examiner—Alton D. Rollins
Attorney, Agent, or Firm—Hammond & Littell, Weissenberger and Muserlian

[57] ABSTRACT

Compounds of the formula

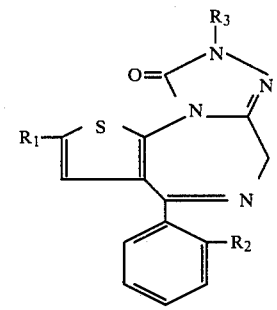

wherein
$R_1$ is chlorine, bromine or iodine,
$R_2$ is hydrogen or halogen, and
$R_3$ is hydrogen, lower alkyl or hydroxy-lower alkyl, or when $R_3$ is hydrogen, an alkali metal salt thereof; the compounds and their salts are useful as anxiolytics, anticonvulsives and sedatives.

3 Claims, No Drawings

8-HALO-6-PHENYL-4H-S-TRIAZOLO (3,4-C) THIENO 1,4-DIAZEPIN-1-ONES

This is a continuation of co-pending U.S. patent application Ser. No. 101,232, filed Dec. 7, 1979, now abandoned, which in turn is a continuation of U.S. patent application Ser. No. 41,941, filed May 24, 1979, now abandoned, which in turn is a continuation of U.S. patent application Ser. No. 881,851, filed Feb. 27, 1978, now abandoned.

This invention relates to novel 8-halo-6-phenyl-4H-s-triazolo[3,4-c]thieno[2,3-e]1,4-diazepin-1-ones and to methods of preparing these compounds.

More particularly, the present invention relates to a novel class of compounds represented by the formula

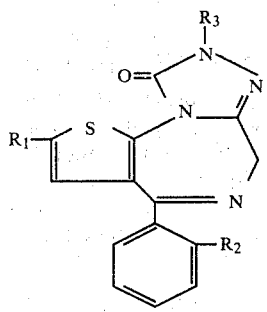

wherein
$R_1$ is chlorine, bromine or iodine
$R_2$ is hydrogen or halogen, and
$R_3$ is hydrogen, lower alkyl or hydroxy-lower alkyl, or, when $R_3$ is hydrogen, an alkali metal salt thereof.

The compounds embraced by formula I above may be prepared by the following methods:

Method A

By mild hydrolysis of a 1-alkoxy-8-halo-6-phenyl-4H-s-triazolo[3,4-c]thieno[2,3-e]1,4-diazepine of the formula

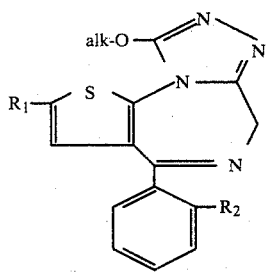

wherein $R_1$ and $R_2$ have the same meanings as in formula I, and alk is lower alkyl.

The hydrolysis is effected in an acid medium, preferably with a hydrohalic acid, at a temperature between room temperature and the reflux temperature of the reaction mixture, preferably at the reflux temperature. The starting compound of the formula II may be provided in solution in a lower alkanol or another inert organic solvent, but the hydrolysis can also be carried out in the absence of a solvent.

The starting compounds of the formula II are described in the literature. For instance, they may be prepared by the method disclosed in German Offenlegungsschrift No. 2,430,041, that is, by halogenating a 1-unsubstituted triazolothienodiazepine and subsequently exchanging the 1-halo-substituent for a lower alkoxy-substituent.

Method B

By reacting a 7-halo-5-phenyl-2-hydrazino-3H-[2,3-e]thieno-1,4-diazepine of the formula

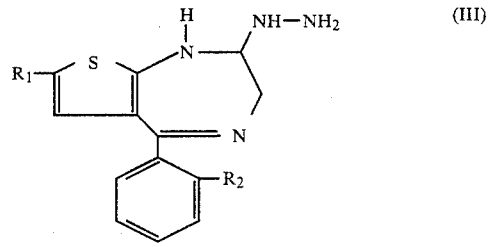

wherein $R_1$ and $R_2$ have the same meanings as in formula I, with phosgene.

The reaction is carried out by dissolving the starting compound of the formula III in an inert solvent, such as toluene, xylene, benzene or a chlorinated hydrocarbon, and adding thereto a solution of phosgene in the same solvent or gaseous phosgene at a temperature between 0° C. and the boiling point of the reaction mixture. Preferably, however, the phosgene is added at room temperature, and the reaction mixture is then gradually heated to its boiling point.

The starting compounds of the formula III are disclosed in German Auslegeschrift No. 2,410,030; they may be preapred by reacting a corresponding 2-mercapto-substituted thienodiazepine with hydrazine.

Those compounds of the formula I wherein $R_3$ is hydrogen may readily be converted into the corresponding compounds where $R_3$ is lower alkyl or hydroxy-lower alkyl by first treating them with sodium hydride, sodium amide or a sodium alcoholate in tetrahydrofuran, dioxane or a lower alkanol to form the corresponding sodium salt. Subsequent reaction of the sodium salt with a conventional alkylating agent, such as an alkyl halide, a dialkylsulfate or a dialkyltosylate, yields the corresponding 2-alkyl-substituted compound; similarly, reaction of the sodium salt with an epoxide yields the corresponding 2-hydroxyalkyl-substituted compound.

The following examples illustrate the present invention and will enable others skilled in the art to understand it more completely. It should be understood, however, that the invention is not limited solely to the particular examples given below.

EXAMPLE 1

8-Bromo-6-(o-chloro-phenyl)-4H-s-triazolo[3,4-c]thieno-[2,3-e]1,4-diazepin-1-one by method A 12.3 gm (0.03 mol) of 8-bromo-6-(o-chloro-phenyl)-1-methoxy-4H-s-triazolo[3,4-c]thieno[2,3-e]1,4-diazepine were refluxed with 300 ml of 48% hydrobromic acid for two hours. Thereafter, the reaction mixture was diluted with 500 ml of water, and the aqueous mixture was allowed to cool. The crystals which separated out were collected by suction filtration and taken up in methylene chloride. The resulting solution was washed with a saturated aqueous sodium bicarbonate solution, dried and evaporated, and the residue was recrystallized from methanol, yielding 10 gm (85% of theory) of the compound of the formula

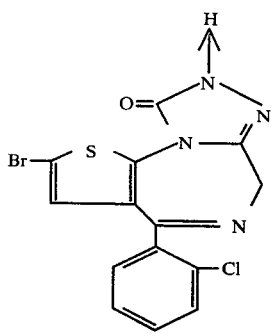

which had a melting point of 235°–238° C.

EXAMPLE 2

Using a procedure analogous to that described in Example 1, 8-chloro-6-(o-chloro-phenyl)-4H-s-triazolo-[3,4-c]thieno[2,3-e]1,4-diazepin-1-one, m.p. 219°–222° C., was prepared from 8-chloro-6-(o-chloro-phenyl)-1-methoxy-4H-s-triazolo[3,4-c]thieno(2,3-e]1,4-diazepine.

EXAMPLE 3

Using a procedure analogous to that described in Example 1, 8-bromo-6-(o-bromo-phenyl)-4H-s-triazolo-[3,4-c]thieno[2,3-e]1,4-diazepin-1-one, m.p. 212°–214° C., was prepared from 8-bromo-6-(o-bromo-phenyl)-1-methoxy-4H-s-triazolo[3,4-c]thieno[2,3-e]1,4-diazepine.

EXAMPLE 4

Using a procedure analogous to that described in Example 1, 8-iodo-6-(O-chloro-phenyl)-4H-s-triazolo-[3,4-c]thieno[2,3-e]1,4-diazepin-1-one, m.p. 215°–217° C., was prepared from 8-iodo-6-(o-chloro-phenyl)-1-methoxy-4H-s-triazolo[3,4-c]thieno[2,3-e]1,4-diazepine.

EXAMPLE 5

Using a procedure analogous to that described in Example 1, 8-chloro-6-phenyl-4H-s-triazolo-[3,4-c]thieno[2,3-e]1,4-diazepin-1-one, m.o. 170°–172° C., was prepared from 8-chloro-6-phenyl-1-methoxy-4H-s-triazolo[3,4-c]thieno[2,3-e]1,4-diazepine.

EXAMPLE 6

8-Bromo-6-(o-chloro-phenyl)-2-methyl-4H-s-triazolo[3,4-c]thieno[2,3-e]1,4-diazepin-1-one 2 gm (0.005 mol) of 8-bromo-6-(o-chloro-phenyl)-4H-s-triazolo[3,4-c]thieno[2,3-e]1,4-diazepine-1-one (the end product of Example 1) were dissolved in 50 ml of tetrahydrofuran, and the solution was gradually admixed with 250 mgm of a 50% sodium hydride dispersion in tetrahydrofuran, and the mixture was stirred for about one hour, whereupon the sodium salt of the starting compound precipitated out. The precipitate was collected, admixed with 3 ml of methyl iodide, and the mixture was stirred for two hours at 60° C. Thereafter, the reaction mixture was evaporated in vacuo, the residue was diluted with water, and the aqueous mixture was extracted with methylene chloride. The organic extract solution was dried and chromatographed on a silicagel column, yielding 1.2 gm (60% of theory) of the compound of the formula

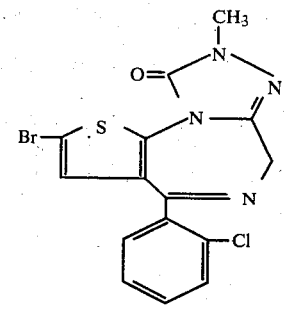

which had a melting point of 136°–137° C.

EXAMPLE 7

8-Bromo-6-(o-chloro-phenyl)-2-[β-hydroxy-ethyl]-4H-s-triazolo[3,4-c]thieno[2,3-e]1,4-one 2 gm (0.005 mol) of 8-bromo-6-(o-chloro-phenyl)-4H-s-triazolo[3,4-c]thieno[2,3-e]1,4-diazepine-1-one were dissolved in 50 ml of 95% methanol, 0.1 ml of tetramethylammonium hydroxide and 5 ml of ethylene oxide were added to the solution, and the mixture was allowed to stand at room temperature for one week. Thereafter, the reaction mixture was evaporated in vacuo, the residue was taken up in methylene chloride, and the solution was chromatographed on a silicagel column. Elution with methylene chloride containing 2% methanol yielded 0.7 gm (34% of theory) of the compound of the formula

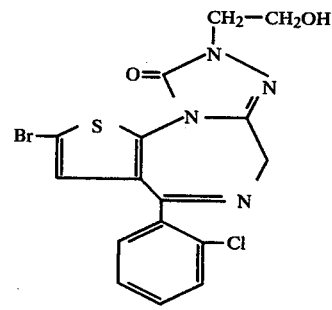

which had a melting point of 112°–115° C.

The compounds embraced by formula I above have useful pharmacodynamic properties. More particularly, they exhibit anxiolytic (anxiety-relieving), anticonvulsive and sedative activities in warm-blooded animals, such as mice and rats, and their toxicity is extraordinarily low.

The above-indicated pharmacological activities of the compounds of this invention were ascertained by the standard test methods described below, and the table shows the results obtained for a representative specie of the genus, namely the end product of Example 1.

Albino mice (NMRI) having a body weight of 20 to 25 gm or albino rats (FW49) having a body weight of 140 to 200 gm were used for the tests, and the test compound was in all cases administered perorally in suspension in olive oil by means of an esophageal sound.

1. Pentetrazole antagonism

Determination of the dose of the test compounds ($ED_{50}$), which counteracts the lethal effect of 125 mgm/kg of pentylene tetrazole in 50% of the animals. The pentylene tetrazole is administered intraperitoneally one hour after administration of the test compound [see M. I. Gluckmann, Curr. Ther. Res. 7, 721 (1965)].

2. Conflict situation (inhibition of passive avoidance)

Determination of the dose of the test compound ($DT_{10}$) at which the test animals in a conflict situation depress a lever ten times to receive a food pellet, even though a simultaneous visual signal indicates to them that they will also receive an electrical shock at the same time [see J. Geller, Arch. Int. Pharmacodyn. 149, 243 (1964)].

3. Acute toxicity

Determination of the median lethal dose ($LD_{50}$), i.e. the dose which causes 50% of the test animals to die [Litchfield and Wilcoxon, J. Phamacol. Exper. Therap. 96,99 (1949)].

The values shown in the following table are graphically determined.

| Compound of Example | Pentetrazole antagonism mouse $ED_{50}$mgm/kg | Pentetrazole antagonism rat $ED_{50}$mgm/kg | Conflict situation rat $DT_{10}$mgm/kg | $LD_{50}$ mouse mgm/kg |
|---|---|---|---|---|
| 1 | 0.37 | 1.9 | 1.25 | >2000 |

For pharmaceutical purposes the compounds of the present invention are administered to warm-blooded animals peorally, parenterally or rectally as active ingredients in customary dosage unit compositions, that is, compositions in dosage unit form consisting essentially of an inert pharmaceutical carrier and one effective dosage unit of the active ingredient, such as tablets, coated pills capsules, wafers, powers, solutions, suspension, emulsions, syrups, suppositories and the like. One effective oral dosage unit of the compounds according to the present invention is from 0.0016 to 0.83 mgm/kg body weight, preferably 0.083 to 0.42 mgm/kg body weight. The daily dose rate is from 0.083 to 2.5 mgm/kg.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:
1. 8-Bromo-6-(o-chlorophenyl)-4H-s-triazolo[3,4-c]thieno[2,3-e]1,4-diazepin-1-one.
2. An amxyolytic, anticonvulsive or sedative pharmaceutical dosage unit composition consisting essentially of an inert pharmaceutical carrier and an effective anxiolytic, anticonvulsive or sedative amount of the compound of claim 1.
3. The method of relieving anxiety, suppressing convulsions or allaying excitement in a warm-blooded animal in need thereof, which comprises perorally, parenterally or rectally administering to said animal an effective anxiolytic, anticonvulsive or sedative amount of the compound of claim 1.

* * * * *

UNITED STATES PATENT AND TRADEMARK OFFICE
CERTIFICATE OF CORRECTION

PATENT NO. : 4,333,944
DATED : June 8, 1982
INVENTOR(S) : KARL-HEINZ WEBER et al.

It is certified that error appears in the above—identified patent and that said Letters Patent is hereby corrected as shown below:

Column 4, line 19, should read:

-- s-triazolo[3,4-c]thieno[2,3-e]1,4-diazepin-1-one --.

Column 6, line 21, "amxyolytic" should read -- anxiolytic --.

Signed and Sealed this

Fourteenth Day of September 1982

[SEAL]

Attest:

Attesting Officer

GERALD J. MOSSINGHOFF

Commissioner of Patents and Trademarks